United States Patent
Mao et al.

(10) Patent No.: US 6,919,430 B1
(45) Date of Patent: Jul. 19, 2005

(54) POLYPEPTIDE—HUMAN GALECTIN 15 AND A POLYNUCLEOTIDE ENCODING THE SAME

(75) Inventors: Yumin Mao, Shanghai (CN); Yi Xie, Shanghai (CN)

(73) Assignee: Shanghai Bio Road Gene Development, Ltd., Shanghai (CN)

( * ) Notice: Subject to any disclaimer, the term of this patent is extended or adjusted under 35 U.S.C. 154(b) by 134 days.

(21) Appl. No.: 10/111,552

(22) PCT Filed: Oct. 27, 2000

(86) PCT No.: PCT/CN00/00376

§ 371 (c)(1),
(2), (4) Date: Sep. 12, 2002

(87) PCT Pub. No.: WO01/30837

PCT Pub. Date: May 3, 2001

(30) Foreign Application Priority Data

Oct. 28, 1999 (CN) ........................................ 99119900 A (51) Int. Cl.[7] .......................... C07K 14/00; A61K 31/00
(52) U.S. Cl. .................................... 530/350; 424/185.1
(58) Field of Search ........................ 435/69.1; 530/350; 424/185.1

(56) References Cited

U.S. PATENT DOCUMENTS 5,837,493 A * 11/1998 Hillman et al. ............ 435/69.1
5,869,289 A    2/1999 Hawkins et al.

FOREIGN PATENT DOCUMENTS

| CN | 1303940 A | * 10/1999 |
| WO | 98/15624 | 4/1998 |
| WO | 98/22139 | 5/1998 |
| WO | 98/32851 | 7/1998 |
| WO | 99/10490 | 3/1999 |

OTHER PUBLICATIONS

Ackerman et al. Journal of Immunology 150, 456–468, 1993.*

* cited by examiner

*Primary Examiner*—Karen Cochrane Carlson
*Assistant Examiner*—Anand Desai
(74) *Attorney, Agent, or Firm*—Crowell & Moring LLP (57) ABSTRACT

The present invention discloses a novel polypeptide-human galectin 15 and a polynucleotide encoding the same, as well as a method of producing the polypeptide by DNA recombinant technology. The present invention also discloses methods of using the polypeptide in treatment of various diseases, such as malignant tumor, blood disease, HIV infection, immunological disease and various inflammations. The present invention also discloses an antagonist against the polypeptide and the therapeutic use of the same.

3 Claims, 2 Drawing Sheets

Identity = 69/138 (50%), Similarity = 94/138 (68%)

```
Human galectin 15:    1 MSSLPVPYTLPVSLPVGSCVIITGTPILTFVKDPQLEVNFYTGMDEDSDIAFQFRLHFGH  60
                        MS LPVPYT   SL GS V I G P++  F+  +P L+V+F+T M E+SDI F F++ FG
Human galectin 10:    1 MSLLPVPYTEAASLSTGSTVTIKGRPLVCFLNEPYLQVDFHTEMKEESDIVFHFQVCFGR  60

Human galectin 15:   61 PAIMNSCVFGIWRYEEKCYYLPFEDGKPFELCIYVRHKEYKVMVNGQRIYNFAHRFPPAS 120
                        +MNS  +G W+ + +   +PF+DG+ FEL I V   +Y+VMVNGQ  Y F HR  P  +
Human galectin 10:   61 RVVMNSREYGAWKQQVESKNMPFQDGQEFELSISVLPDKYQVMVNGQSSYTFDHRIKPEA 120

Human galectin 15:  121 VKMLQVFRDISLTRVLIS                                           138
                        VKM+QV+RDISLT+ +S
Human galectin 10:  121 VKMVQVWRDISLTKFNVS                                           138
```

POLYPEPTIDE— HUMAN GALECTIN 15 AND A POLYNUCLEOTIDE ENCODING THE SAME

This application is a 35 U.S.C. 371 of PCT/CN00/00376, filed Oct. 27, 2000 which claims priority to Chinese application 99119900.6, filed Oct. 28, 1999.

FIELD OF INVENTION

The invention relates to the field of biotechnology. In particular, the invention relates to a novel polypeptide, human galectin 15, and a polynucleotide sequence encoding said polypeptide. The invention also relates to the method for the preparation and use of said polynucleotide and polypeptide.

TECHNICAL BACKGROUND

CLC (Charcot-Leyden Crystal) protein, or eosinophil leukocyte lysophospholipase, is a typical protein of human eosinophil leukocytes and basophiles. Recently it has been shown that CLC protein is structurally and functionally related to the galectin family of beta-galactoside binding proteins. The galectin family of proteins share several common characteristics, such as a linear ligand-binding site (coded by an exon). In addition, the genes encoding the CLC protein gene is structurally similar to genes encoding galectin.

Galectins are in turn a member of the animal beta-galactoside-binding lectin family. In mammals lectins are classified into four types: type C, type P, pentraxins and galectins. Galectins are sulfhydryl dependent, and specifically bind to beta-galactoside). Galectins can be further divided into two types, type S and type S-Lac. Galectins are defined by two essential biochemical characteristics: 1) a unique and conserved amino acid sequence, and 2) affinity with beta-galactose. The coding sequence of a CLC protein gene has four exons, including a highly conserved beta-galactoside binding site encoded by exon III, i.e., a carbohydrate binding domain. CLC protein is a single peptide and is secreted to the cytoplasm after synthesis. It is a soluble protein, secreted through non-typical pathway. All above-mentioned are typical characteristics of galectin. Therefore, we consider the novel protein of the invention a member of galectin family, and name it as human galectin 15.

OBJECTIVES OF THE INVENTION

One objective of the invention is to provide an isolated novel polypeptide, i.e., a human galectin 15, and fragments, analogues and derivatives thereof.

Another objective of the invention is to provide a polynucleotide encoding said polypeptide.

Another objective of the invention is to provide a recombinant vector containing a polynucleotide encoding a human galectin 15.

Another objective of the invention is to provide a genetically engineered host cell containing a polynucleotide encoding a human galectin 15.

Another objective of the invention is to provide a method for producing a human galectin 15.

Another objective of the invention is to provide an antibody against a human galectin 15 of the invention.

Another objective of the invention is to provide mimetics, antagonists, agonists, and inhibitors for the polypeptide of the human galectin 15.

Another objective of the invention is to provide a method for the diagnosis and treatment of the diseases associated with an abnormality of human galectin 15.

SUMMARY OF THE INVENTION

In the first aspect, the invention provides a novel, isolated human galectin 15 which is originated from human and comprises a polypeptide having the amino acid sequence of SEQ ID NO: 2, or its conservative mutants, or its active fragments, or its active derivatives and its analogues. Preferably, the polypeptide is a polypeptide having the amino acid sequence of SEQ ID NO: 2.

In the second aspect, the invention provides an isolated polynucleotide encoding said polypeptide, the polynucleotide comprises a nucleotide sequence that shares at least 70% homology to the nucleotide sequence selected from the group consisting of (a) the polynucleotide encoding said human galectin 15; and (b) a polynucleotide complementary to the polynucleotide (a). Preferably, said nucleotide sequence encodes a polypeptide comprising the amino acid sequence of SEQ ID NO: 2. More preferably, said nucleotide sequence is selected from the group consisting of (a) the sequence of position 225–644 in SEQ ID NO: 1; and (b) the sequence of position 1–775 in SEQ ID NO: 1.

In the third aspect, the invention provides a vector comprising said polynucleotide and a host cell transformed or transfected by said vector or directly transformed or transfected by said polynucleotide.

Other aspects of the invention are apparent to the skilled in the art in view of the disclosure.

BRIEF DESCRIPTION OF THE DRAWINGS

The following drawings are provided to illustrate the embodiment of the invention, not to limit the scope of invention defined by the claims.

DETAILED DESCRIPTION OF THE INVENTION

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been isolated from other components naturally accompanying them, they are isolated or purified.

As used herein, "isolated human galectin 15," means that human galectin 15, does not essentially contain other proteins, lipids, carbohydrate or any other substances associated therewith in nature. The skilled in the art can purify human galectin 15, by standard protein purification techniques. The purified polypeptide forms a single main band on a non-reductive PAGE gel. The purity of human galectin 15 can be analyzed by amino acid sequence analysis.

The invention provides a novel polypeptide—human galectin 15, which comprises the amino acid sequence shown in SEQ ID NO: 2. The polypeptide of the invention may be a recombinant polypeptide, natural polypeptide, or synthetic polypeptide, preferably a recombinant polypeptide. The polypeptide of the invention may be a purified natural product or a chemically synthetic product. Alternatively, it may be produced from prokaryotic or eukaryotic hosts, such as bacterial, yeast, higher plant, insect, and mammal cells, using recombinant techniques. Depending on the host used in the protocol of recombinant production, the polypeptide of the invention may be glycosylated or non-glycosylated. The polypeptide of the invention may or may not comprise the starting Met residue.

The invention further comprises fragments, derivatives and analogues of human galectin 15. As used in the invention, the terms "fragment", "derivative" and "analogue" mean the polypeptide that essentially retains the same biological functions or activity of human galectin 15 of the invention. The fragment, derivative or analogue of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues are substituted with other residues, include a substituent group; or (iii) one in which the mature polypeptide is fused with another compound, such as a compound to increase the half-life of the polypeptide (for example, polyethylene glycol); or (iv) one in which additional amino acids are fused to the mature polypeptide, such as a leader or secretory sequence or a sequence which is employed for purification of the mature polypeptide or a proprotein sequence. Such fragments, derivatives and analogs are deemed to be within the scope of the skilled in the art from the teachings herein.

The invention provides an isolated nucleic acid or polynucleotide which comprises the polynucleotide encoding an amino acid sequence of SEQ ID NO: 2. The polynucleotide sequence of the invention includes the nucleotide sequence of SEQ ID NO: 1. The polynucleotide of the invention was identified in a human embryonic brain cDNA library. Preferably, it comprises a full-length polynucleotide sequence of 775 bp, whose ORF (225–644) encodes 139 amino acids. Based on amino acid homology comparison, it is found that the encoded polypeptide is 50% homologous to (human galectin). This novel human human galectin 15 has similar structures and biological functions to those of the (human galectin).

The polynucleotide according to the invention may be in the forms of DNA or RNA. The forms of DNA include cDNA, genomic DNA, and synthetic DNA, etc., in single stranded or double stranded form. DNA may be an encoding strand or non-encoding strand. The coding sequence for mature polypeptide may be identical to the coding sequence shown in SEQ ID NO: 1, or is a degenerate sequence. As used herein, the term "degenerate sequence" means an sequence which encodes a protein or peptide comprising a sequence of SEQ ID NO: 2 and which has a nucleotide sequence different from the sequence of coding region in SEQ ID NO: 1.

The polynucleotide encoding the mature polypeptide of SEQ ID NO: 2 includes those encoding only the mature polypeptide, those encoding mature polypeptide plus various additional coding sequence, the coding sequence for mature polypeptide (and optional additional encoding sequence) plus the non-coding sequence.

The term "polynucleotide encoding the polypeptide" includes polynucleotides encoding said polypeptide and polynucleotides comprising additional coding and/or non-coding sequences.

The invention further relates to variants of the above polynucleotides which encode a polypeptide having the same amino acid sequence of invention, or a fragment, analogue and derivative of said polypeptide. The variant of the polynucleotide may be a naturally occurring allelic variant or a non-naturally occurring variant. Such nucleotide variants include substitution, deletion, and insertion variants. As known in the art, an allelic variant may have a substitution, deletion, and insertion of one or more nucleotides without substantially changing the functions of the encoded polypeptide.

The present invention further relates to polynucleotides, which hybridize to the hereinabove-described sequences, that is, there is at least 50% and preferably at least 70% identity between the sequences. The present invention particularly relates to polynucleotides, which hybridize to the polynucleotides of the invention under stringent conditions. As herein used, the term "stringent conditions" means the following conditions: (1) hybridization and washing under low ionic strength and high temperature, such as 0.2×SSC, 0.1% SDS, 60° C.; or (2) hybridization after adding denaturants, such as 50% (v/v) formamide, 0.1% bovine serum/0.1% Ficoll, 42° C.; or (3) hybridization only when the homology of two sequences at least 95%, preferably 97%. Further, the polynucleotides which hybridize to the hereinabove described polynucleotides encode a polypeptide which retains the same biological function and activity as the mature polypeptide of SEQ ID NO: 2

The invention also relates to nucleic acid fragments hybridized with the hereinabove sequence. As used in the present invention, the length of the "nucleic acid fragment" is at least more than 10 bp, preferably at least 20–30 bp, more preferably at least 50–60 bp, and most preferably at least 100 bp. The nucleic acid fragment can be used in amplification techniques of nucleic acid, such as PCR, so as to determine and/or isolate the polynucleotide encoding human galectin 15.

The polypeptide and polynucleotide of the invention are preferably in the isolated form, preferably purified to be homogenous.

According to the invention, the specific nucleic acid sequence encoding human galectin 15 can be obtained in various ways. For example, the polynucleotide is isolated by hybridization techniques well-known in the art, which include, but are not limited to 1) the hybridization between a probe and genomic or cDNA library so as to select a homologous polynucleotide sequence, and 2) antibody screening of expression library so as to obtain polynucleotide fragments encoding polypeptides having common structural features.

According to the invention, DNA fragment sequences may further be obtained by the following methods: 1) isolating double-stranded DNA sequence from genomic DNA; and 2) chemical synthesis of DNA sequence so as to obtain the double-stranded DNA.

Among the above methods, the isolation of genomic DNA is least frequently used. A commonly used method is the direct chemical synthesis of DNA sequence. A more frequently used method is the isolation of cDNA sequence. Standard methods for isolating the cDNA of interest is to isolate mRNA from donor cells that highly express said gene followed by reverse transcription of mRNA to form plasmid or phage cDNA library. There are many established techniques for extracting mRNA and the kits are commercially available (e.g. Qiagene). Conventional method can be used to construct cDNA library (Sambrook, et al., Molecular Cloning, A Laboratory Manual, Cold Spring Harbor Laboratory. New York, 1989). The cDNA libraries are also commercially available. For example, Clontech Ltd. has various cDNA libraries. When PCR is further used, even an extremely small amount of expression products can be cloned.

Numerous well-known methods can be used for screening for the polynucleotide of the invention from cDNA library. These methods include, but are not limited to, (1) DNA-DNA or DNA-RNA hybridization; (2) the appearance or loss of the function of the marker-gene; (3) the determination of the level of human galectin 15 transcripts; (4) the determination of protein product of gene expression by immunology methods or the biological activity assays. The above methods can be used alone or in combination.

In method (1), the probe used in the hybridization could be homologous to any portion of polynucleotide of invention. The length of probe is typically at least 10 nucleocides, preferably at least 30 nucleocides, more preferably at least 50 nucleocides, and most preferably at least 100 nucleotides. Furthermore, the length of the probe is usually less than 2000 nucleotides, preferably less than 1000 nucleotides. The probe usually is the DNA sequence chemically synthesized on the basis of the sequence information. Of course, the gene of the invention itself or its fragment can be used as a probe. The labels for DNA probe include, e.g., radioactive isotopes, fluoresceins or enzymes such as alkaline phosphatase.

In method (4), the detection of the protein products expressed by human galectin 15 gene can be carried out by immunology methods, such as Western blotting, radioimmunoassay, and ELISA.

The method of amplification of DNA/RNA by PCR (Saiki, et al. Science 1985; 230:1350–1354) is preferably used to obtain the polynucleotide of the invention. Especially when it is difficult to obtain the full-length cDNA, the method of RACE (RACE- cDNA terminate rapid amplification) is preferably used. The primers used in PCR can be selected according to the polynucleotide sequence information of the invention disclosed herein, and can be synthesized by conventional methods. The amplified DNA/RNA fragments can be isolated and purified by conventional methods such as gel electrophoresis.

Sequencing of polynucleotide sequence of the gene of the invention or its various DNA fragments can be carried out by the conventional dideoxy sequencing method (Sanger et al. PNAS, 1977, 74: 5463–5467). Sequencing of polynucleotide sequence can also be carried out using the commercially available sequencing kits. In order to obtain the full-length cDNA sequence, it is necessary to repeat the sequencing process. Sometimes, it is needed to sequence the cDNA of several clones to obtain the full-length cDNA sequence.

The invention further relates to a vector comprising the polynucleotide of the invention, a genetically engineered host cell transformed with the vector of the invention or directly with the sequence encoding human galectin 15, and a method for producing the polypeptide of the invention by recombinant techniques.

In the present invention, the polynucleotide sequences encoding human galectin 15 may be inserted into a vector to form a recombinant vector containing the polynucleotide of the invention. The term "vector" refers to a bacterial plasmid, bacteriophage, yeast plasmid, plant virus or mammalian virus such as adenovirus, retrovirus or any other vehicle known in the art. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J Biol. Chem., 263:3521, 1988) and baculovirus-derived vectors for expression in insect cells. Any plasmid or vector can be used to construct the recombinant expression vector as long as it can replicate and is stable in the host. One important feature of an expression vector is that the expression vector typically contains an origin of replication, a promoter, a marker gene as well as translation regulatory components.

Methods known in the art can be used to construct an expression vector containing the DNA sequence of human galectin 15 and appropriate transcription/translation regulatory components. These methods include in vitro recombinant DNA technique, DNA synthesis technique, in vivo recombinant technique and so on (Sambroook, et al. Molecular Cloning, a Laboratory Manual, cold Spring Harbor Laboratory. New York, 1989). The DNA sequence is operatively linked to a proper promoter in an expression vector to direct the synthesis of mRNA. Exemplary promoters are lac or trp promoter of $E.$ $coli$; $P_L$ promoter of $\lambda$ phage; eukaryotic promoters including CMV immediate early promoter, HSV thymidine kinase promoter, early and late SV40 promoter, LTRs of retrovirus, and other known promoters which control gene expression in the prokaryotic cells, eukaryotic cells or viruses. The expression vector may further comprise a ribosome binding site for initiating translation, transcription terminator and the like. Transcription in higher eukaryotes is increased by inserting an enhancer sequence into the vector. Enhancers are cis-acting elements of DNA, usually about from 10 to 300 bp in length that act on a promoter to increase gene transcription level. Examples include the SV40 enhancer on the late side of the replication origin 100 to 270 bp, the polyoma enhancer on the late side of the replication origin, and adenovirus enhancers.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for $E.$ $coli$.

The skilled in the art know clearly how to select appropriate vectors, transcriptional regulatory elements, e.g., promoters, enhancers, and selective marker genes.

According to the invention, polynucleotide encoding human galectin 15 or recombinant vector containing said polynucleotide can be transformed or transfected into host cells to construct genetically engineered host cells containing said polynucleotide or said recombinant vector. The term "host cell" means prokaryote, such as bacteria; or primary eukaryote, such as yeast; or higher eukaryotic, such as mammalian cells. Representative examples are bacterial cells, such as $E.$ $coli,$ $Streptomyces,$ $Salmonella$ $typhimurium;$ fungal cells, such as yeast; plant cells; insect cells such as Drosophila S2 or Sf9; animal cells such as CHO, COS or Bowes melanoma.

Transformation of a host cell with the DNA sequence of invention or a recombinant vector containing said DNA sequence may be carried out by conventional techniques as are well known to those skilled in the art. When the host is prokaryotic, such as $E.$ $coli,$ competent cells, which are capable of DNA uptake, can be prepared from cells harvested after exponential growth phase and subsequently treated by the CaCl$_2$ method using procedures well known in the art. Alternatively, MgCl$_2$ can be used. Transformation can also be carried out by electroporation, if desired. When the host is an eukaryote, transfection methods as well as calcium phosphate precipitation may be used. Conventional mechanical procedures such as micro-injection, electroporation, or liposome-mediated transfection may also be used.

The recombinant human galectin 15 can be expressed or produced by the conventional recombinant DNA technology (Science, 1984; 224:1431), using the polynucleotide sequence of the invention. The steps generally include:

(1) transfecting or transforming the appropriate host cells with the polynucleotide (or variant) encoding human human galectin 15 of the invention or the recombinant expression vector containing said polynucleotide;

(2) culturing the host cells in an appropriate medium; and (3) isolating or purifying the protein from the medium or cells.

In Step (2) above, depending on the host cells used, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In Step (3), the recombinant polypeptide may be included in the cells, or expressed on the cell membrane, or secreted out of the cell. If desired, physical, chemical and other properties can be utilized in various isolation methods to isolate and purify the recombinant protein. These methods are well-known to those skilled in the art and include, but are not limited to conventional renaturation treatment, treatment by a protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatography, and a combination thereof.

The recombinant galectin 15 protein or polypeptide uses widely. Galectin 15 plays an important role in physiology, growth and pathology of human being. Such uses include, but not limited to, treating directly as a medicine the disease caused by the lower or lost function of galectin 15 protein, screening an antibody, polypeptide or other ligand of accelerating or antagonizing the galectin 15 protein. For example, the antibody activating or inhibiting the function of galectin 15 protein. The expressed recombinant galectin 15 protein screening polypeptide library is used for searching the polypeptide, which is medicative and inhibits or stimulated the function of galectin 15 protein.

The invention also provides methods for screening compounds so as to identify an agent which enhances human galectin 15 activity (agonists) or decrease human galectin 15 activity (antagonists). The agonists enhance the biological functions of human galectin 15 such as inactivation of cell proliferation, while the antagonists prevent and cure the disorders associated with the excess cell proliferation, such as various cancers. For example, in the presence of an agent, the mammal cells or the membrane preparation expressing human galectin 15 can be incubated with the labeled human galectin 15 to determine the ability of the agent to enhance or repress the interaction.

Antagonists of human galectin 15 include antibodies, compounds, receptor deletants and analogues. The antagonists of human galectin 15 can bind to human galectin 15 and eliminate or reduce its function, or inhibit the production of human galectin 15, or bind to the active site of said polypeptide so that the polypeptide can not function biologically.

When screening for compounds as an antagonist, human galectin 15 may be added into a biological assay. It can be determined whether the compound is an antagonist or not by determining its effect on the interaction between human galectin 15 and its receptor. Using the same method as that for screening compounds, receptor deletants and analogues acting as antagonists can be selected. Polypeptide molecules capable of binding to human galectin 15 can be obtained by screening a polypeptide library comprising various combinations of amino acids bound onto a solid matrix. Usually, human galectin 15 is labeled in the screening.

The invention further provides a method for producing antibodies using the polypeptide, and its fragment, derivative, analogue or cells as an antigen. These antibodies may be polyclonal or monoclonal antibodies. The invention also provides antibodies against epitopes of human galectin 15. These antibodies include, but are not limited to, polyclonal antibody, monoclonal antibody, chimeric antibody, single-chain antibody, Fab fragment and the fragments produced by a Fab expression library.

Polyclonal antibodies can be prepared by immunizing animals, such as rabbit, mouse, and rat, with human galectin 15. Various adjuvants, including but are not limited to Freund's adjuvant, can be used to enhance the immunization. The techniques for producing human galectin 15 monoclonal antibodies include, but are not limited to, the hybridoma technique (Kohler and Milstein. Nature,1975, 256:495–497), the trioma technique, the human B-cell hybridoma technique, the EBV-hybridoma technique and so on. A chimeric antibody comprising a constant region of human origin and a variable region of non-human origin can be produced using methods well-known in the art (Morrison et al, PNAS,1985,81:6851). Furthermore, techniques for producing a single-chain antibody (U.S. Pat. No. 4,946,778) are also useful for preparing single-chain antibodies against human galectin 15.

The antibody against human galectin 15 can be used in immunohistochemical method to detect the presence of human galectin 15 in a biopsy specimen.

The monoclonal antibody specific to human galectin 15 can be labeled by radioactive isotopes, and injected into human body to trace the location and distribution of human galectin 15. This radioactively labeled antibody can be used in the non-wounding diagnostic method for the determination of tumor location and metastasis.

Antibodies can also be designed as an immunotoxin targeting a particular site in the body. For example, a monoclonal antibody having high affinity to human galectin 15 can be covalently bound to bacterial or plant toxins, such as diphtheria toxin, ricin, ormosine. One common method is to challenge the amino group on the antibody with sulfydryl cross-linking agents, such as SPDP, and bind the toxin onto the antibody by interchanging the disulfide bonds. This hybrid antibody can be used to kill human galectin 15-positive cells.

The antibody of the invention is useful for the therapy or the prophylaxis of disorders related to the human galectin 15. The appropriate amount of antibody can be administrated to stimulate or block the production or activity of human galectin 15.

The invention further provides diagnostic assays for quantitative and in situ measurement of human galectin 15 level.

These assays are well known in the art and include FISH assay and radioimmunoassay. The level of human galectin 15 detected in the assay can be used to illustrate the importance of human galectin 15 in diseases and to determine the diseases associated with human galectin 15.

The polypeptide of the invention is useful in the analysis of polypeptide profile. For example, the polypeptide can be specifically digested by physical, chemical, or enzymatic means, and then analyzed by one, two or three dimensional gel electrophoresis, preferably by spectrometry.

New human galectin 15 polynucleotides also have many therapeutic applications. Gene therapy technology can be used in the therapy of abnormal cell proliferation, development or metabolism, which are caused by the loss of human galectin 15 expression or the abnormal or non-active expression of human galectin 15. Recombinant gene therapy vectors, such as virus vectors, can be designed to express mutated human galectin 15 so as to inhibit the activity of endogenous human galectin 15. For example, one form of mutated human galectin 15 is a truncated human galectin 15 whose signal transduction domain is deleted. Therefore, this mutated human galectin 15 can bind the downstream substrate without the activity of signal transduction. Thus, the recombinant gene therapy vectors can be used to cure diseases caused by abnormal expression or activity of human galectin 15. The expression vectors derived from a virus, such as retrovirus, adenovirus, adeno-associated virus, herpes simplex virus, parvovirus, and so on, can be used to introduce the human galectin 15 gene into the cells. The methods for constructing a recombinant virus vector harboring human galectin 15 gene are described in the literature (Sambrook, et al. supra). In addition, the recombinant human galectin 15 gene can be packed into hposome and then transferred into the cells.

The methods for introducing the polynucleotides into tissues or cells include directly injecting the polynucleotides into tissue in the body; or introducing the polynucleotides into cells in vitro with vectors, such as virus, phage, or plasmid, etc, and then transplanting the cells into the body.

Also included in the invention are ribozyme and the oligonucleotides, including antisense RNA and DNA, which inhibit the translation of the human galectin 15 mRNA. Ribozyme is an enzyme-like RNA molecule capable of specifically cutting certain RNA. The mechanism is nucleic acid endo-cleavage following specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding said RNA, wherein said DNA sequence is integrated into the vector and downstream of the RNA polymerase promoter. In order to increase its stability, a nucleic acid molecule can be modified in many manners, e.g., increasing the length of two the flanking sequences, replacing the phosphodiester bond with the phosphothioester bond in the oligonucleotide.

The polynucleotide encoding human galectin 15 can be used in the diagnosis of human galectin 15 related diseases. The polynucleotide encoding human galectin 15 can be used to detect whether human galectin 15 is expressed or not, and whether the expression of human galectin 15 is normal or abnormal in the case of diseases. For example, human galectin 15 DNA sequences can be used in the hybridization with biopsy samples to determine the expression of human galectin 15. The hybridization methods include Southern blotting, Northern blotting and in situ blotting, etc., which are well-known and established techniques. The corresponding kits are commercially available. A part of or all of the polynucleotides of the invention can be used as probe and fixed on a microarray or DNA chip for analysis of differential expression of genes in tissues and for the diagnosis of genes. The human galectin 15 specific primers can be used in RNA-polymerase chain reaction and in vitro amplification to detect transcripts of human galectin 15.

Further, detection of mutations in human galectin 15 gene is useful for the diagnosis of human galectin 15 -related diseases. Mutations of human galectin 15 include site mutation, translocation, deletion, rearrangement and any other mutations compared with the wild-type human galectin 15 DNA sequence. The conventional methods, such as Southern blotting, DNA sequencing, PCR and in situ blotting, can be used to detect a mutation. Moreover, mutations sometimes affects the expression of protein. Therefore, Northern blotting and Western blotting can be used to indirectly determine whether the gene is mutated or not.

Sequences of the present invention are also valuable for chromosome identification. The sequence is specifically targeted to and can hybridize with a particular location on an individual human chromosome. There is a current need for identifying particular sites of gene on the chromosome. Few chromosome marking reagents based on actual sequence data (repeat polymorphism) are presently available for marking chromosomal location. The mapping of DNA to chromosomes according to the present invention is an important first step in correlating those sequences with genes associated with disease.

Briefly, sequences can be mapped to chromosomes by preparing PCR primers (preferably 15–35 bp) from the cDNA. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the oligonucleotide primers of the invention, sublocalization can be achieved with panels of fragments from specific chromosomes or pools of large genomic clones in an analogous manner.

Other mapping strategies that can similarly be used to map to its chromosome include in situ hybridization, pre-screening with labeled flow-sorted chromosomes and pre-selection by hybridization to construct chromosome specific-cDNA libraries.

Fluorescence in situ hybridization (FISH) of a cDNA clones to a metaphase chromosomal spread can be used to provide a precise chromosomal location in one step. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis.

Next, it is necessary to determine the differences in the cDNA or genomic sequence between affected and unaffected individuals. If a mutation is observed in some or all of the affected individuals but not in any normal individuals, then the mutation is likely to be the cause of the disease. Comparison of affected and unaffected individuals generally involves first looking for structural alterations in the chromosomes, such as deletions or translocations, that are visible from chromosome level, or detectable using PCR based on that DNA sequence. With current resolution of physical mapping and genetic mapping techniques, a cDNA precisely localized to a chromosomal region associated with the disease could be one of 50 to 500 potential causative genes. (This assumes 1 megabase mapping resolution and one gene per 20 kb).

According to the invention, the polypeptides, polynucleotides and its mimetics, agonists, antagonists and inhibitors may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonist, as well as a pharmaceutically acceptable carrier or excipient with no influence on the effect of the drug. These compositions can be used as drugs in disease treatment.

The invention also provides a pharmaceutical pack or kit comprising one or more containers filled with one or more of the ingredients of the pharmaceutical compositions of the invention. With such container(s) there may be a notice from a governmental agency, that regulates the manufacture, use or sale of pharmaceuticals or biological products, the notice reflects government's approval for the manufacture, use or sale for human administration. In addition, the polypeptides of the invention may be employed in conjunction with other therapeutic compounds.

The pharmaceutical compositions may be administered in a convenient manner, such as through topical, intravenous, intraperitoneal, intramuscular, subcutaneous, intranasal or intradermal routes. human galectin 15 is administered in an amount, which is effective for treating and/or prophylaxis of the specific indication. The amount of human galectin 15 administrated on patient will depend upon various factors, such as delivery methods, the subject health, the judgment of the skilled clinician.

EXAMPLES

The invention is further illustrated by the following examples. It is appreciated that these examples are only intended to illustrate the invention, not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

Example 1

Cloning of Human Galectin 15 Gene

Total RNA from a human embryonic brain was extracted by the one-step method with guanidinium isocyanate/phenol/chloroform. The poly(A) mRNA was isolated from the total RNA with Quik mRNA Isolation Kit (Qiegene). cDNA was prepared by reverse transcription with 2 μg poly(A) mRNA. The cDNA fragments were inserted into the polyclonal site of pBSK(+) vector (Clontech) using Smart cDNA cloning kit (Clontech) and then transformed into DH5α to form the cDNA library. The 5'- and 3'-ends of all clones were sequenced with Dye terminate cycle reaction sequencing kit (Perkin- Elmer) and ABI 377 Automatic Sequencer (Perkiin-Elmer). The sequenced cDNA were compared with the public database of DNA sequences (Genebank) and the DNA sequence of one clone 0484E08 was found to be a novel DNA sequence. The inserted cDNA sequence of clone 0484E08 was dual-directionally sequenced with a serial of synthesized primers. It was indicated that the full length cDNA contained in clone 0484E08 was 755bp (SEQ ID NO: 1) with a 419bp ORF located in positions 225–644 which encoded a novel protein (SEQ ID NO: 2). This clone was named pBS-0484E08 and the encoded protein was named human galectin 15.

Example 2

Homology Search of cDNA Clone

The homology research of the DNA sequence and its protein sequence of human galectin 15 of the invention were performed by Blast (Basic local Alignment search tool) (Altschul, SF et al.J.Mol.Biol.1990;215:403–10) in databases such as Genbank, Swissport, etc. The most homologous gene to human galectin 15 of the invention is known (human galectinlo). The Genbank accession number of its encoded protein is AC005393. The alignment result of the protein was shown in FIG. 1. Two proteins are highly homologous with an identity of 50% and a similarity of 68%.

Example 3

Cloning Human Galectin 15 Gene by RT-PCR

The template was total RNA extracted from a human embryonic brain. The reverse transcription was carried out with oligo-dT primer to produce cDNAs. After cDNA purified with Qiagen Kit, PCR was carried out with the following primers:

Primer 1: 5'-GGCTGCATTACAGACACAGACCTG-3' (SEQ ID NO: 3) Primer 2:5'-GTTTGGTGCTGT-PTTAATGATCAT-3' (SEQ ID NO: 4)

Primer 1 is the forward sequence started from position 1 of 5' end of SEQ ID NO: 1.

Primer 2 is the reverse sequence of the 3' end of SEQ ID NO: 1.

The amplification condition was a 50 ul reaction system containing 50 mmol/L KCl, 10mmol/L Tris-Cl (pH8.5), 1.5mmol/L $MgCl_2$, 200umol/L dNTP, 10 pmol of each primer, 1U Taq DNA polymerase(Clontech). The reaction was performed on a PE 9600 DNA amplifier with the following parameters: 94° C. 30 sec, 55° C. 30 sec, and 72° C. 2 min for 25 cycles. β-actin was used as a positive control, and a blank template, as a negative control in RT-PCR. The amplified products were purified with a QIAGEN kit, and linked with a pCR vector (Invitrogen) using a TA Cloning Kit. DNA sequencing results show that the DNA sequence of PCR products was identical to nucleotides 1–775 bp of SEQ ID NO: 1.

Example 4

Northern Blotting of Expression of Human Galectin 15 Gene

Total RNA was extracted by one-step method (Anal. Biochem 1987, 162, 156–159) with guanidinium isocyanate-phenol-chloroform. That is, homogenate the organize using 4M guanidinium isocyanate-25mM sodium citrate, add 1 volume phenol and ⅕ volume chloroform-isoamyl alcohol(49:1), centrifuge after mixing. Take out the water phase, add 0.8 volume isopropyl alcohol, then centrifuge the mixture. Wash the RNA precipitation using 70% ethanol, then dry, then dissolve it in the water. 20μg RNA was electrophoresed on the 1.2% agarose gel containing 20 mM 3-(N-morpholino) propane sulfonic acid(pH 7.0)-5mM sodium acetate-imM EDTA- 2.2M formaldehyde. Then transfer it to a nitrocellulose filter. Prepare the $^{32}$P-labelled DNA probe with α-$^{32}$P dATP by random primer method. The used DNA probe is the coding sequence (225 bp–644bp) of human galectin 15 amplified by PCR indicated in FIG. 1. The nitrocellulose filter with the transferred RNA was hybridized with the $^{32}$P-labelled DNA probe (2×10$^6$ cpm/ml) overnight in a buffer containing 50% formamide-25mM KH$_2$PO$_4$(Ph7.4)-5×Denhardt's solution and 200μg/ml salmine. Then wash the filter in the 1×SSC-0.1% SDS, at 55° C., for 30 min. Then analyze and quantitative determinate using Phosphor Imager.

Example 5

In vitro Expression, Isolation and Purification of Recombinant Human Galectin 15

Figure 1:
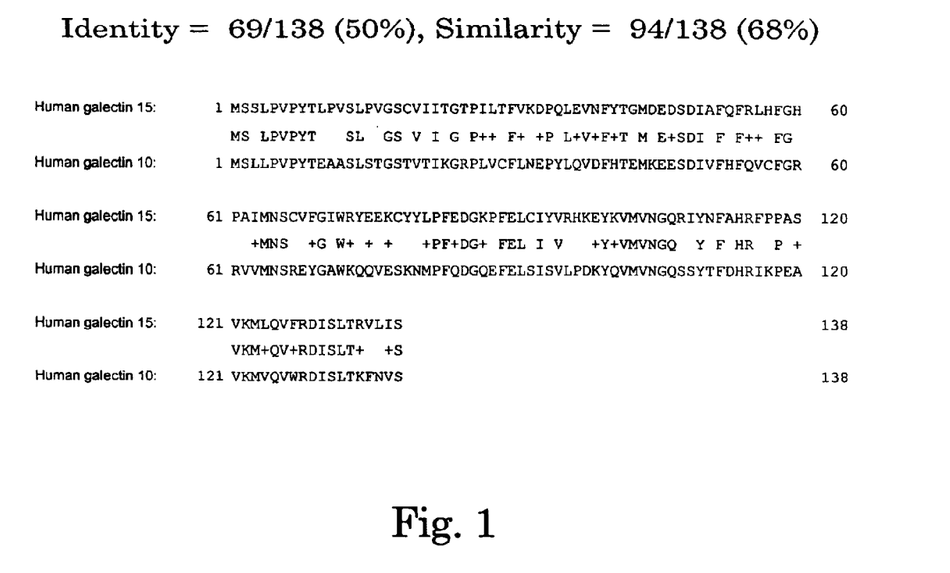
FIG. 1 shows an alignment comparison of amino acid sequences of human galectin 15 of the invention and (human galectin10). The upper sequence is human galectin 15, and the lower sequence is (human galectin10). The identical and similar amino acids are indicated by a one-letter code of amino acid and "+" respectively.

A pair of primers for specific amplification was designed based on SEQ ID NO: 1 and the encoding region in FIG. 1, the sequences are as follows:

Primer3:5'-CCCCCATGGATGTCATCACTACCCGT-ACCATAC-3' (SEQ ID NO: 5)

Primer4:5'-CATGGATCCCCATCGCTGATAAGCA-CTCTGGTC-3' (SEQ ID NO: 6)

These two primers contain a NcoI and BamHI cleavage site on the 5' end respectively. Within the sites are the coding sequences of the 5' and 3' end of the desired gene. NcoI and BamHI cleavage sites were corresponding to the selective cleavage sites on the expression vector pET-28b(+) (Novagen, Cat. No. 69865.3). PCR amplification was performed with the plasmid pBS-0484E08 containing the full-length target gene as a template. The PCR reaction was subject to a 50 μl system containing 10 pg pBS-0484E08 plasmid, 10 pmol of Primer-3 and 10 pmol of Primer-4, 1, μl of Advantage polymerase Mix (Clontech). The parameters of PCR were 94° C. 20 sec, 60° C. 30 sec, and 68° C. 2 min for 25 cycles. After digesting the amplification products and the plasmid pET-28(+) by NcoI and BamHI, the large fragments were recovered and ligated with T4 ligase.

Figure 2:
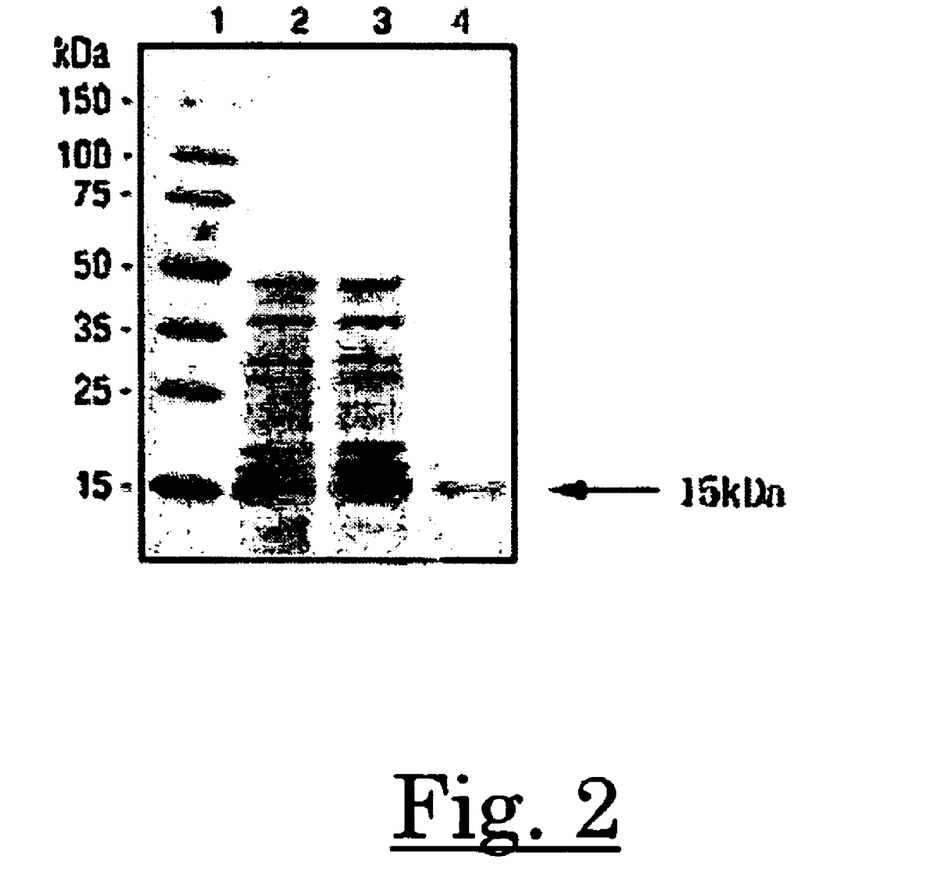
FIG. 2 shows the SDS-PAGE of the isolated human galectin 15,, which has a molecular weight of 15 kDa. The isolated protein band is marked with an arrow.

The ligated product was transformed into *E.coli* DH5α with the calcium chloride method. After cultured overnight on a LB plate containing a final concentration of 30 μg/ml kanamycin, positive clones were selected out using colony PCR and then sequenced. The positive clone pET-(pET-0484E08) with the correct sequence was selected out and the recombinant plasmid thereof was transformed into BL21 (DE3)plySs (Novagen) using the calcium chloride method. In a LB liquid medium containing a final concentration of 30 μg/ml of kanamycin, the host bacteria BL21(pET-0484E08) were cultured at 37° C. to the exponential growth phase, then IPTG were added with the final concentration of 1 mmol/L, the cells were cultured for another 5 hours, and then centrifuged to harvest the bacteria. After the bacteria were sonicated, the supernatant was collected by centrifugation. Then the purified desired protein—human galectin 15 was obtained by a His.Bind Quick Cartridge (Novagen) affinity column with binding 6His-Tag. SDS-PAGE showed a single band at 15 kDa (FIG. 2). The band was transferred onto the PVDF membrane and the N terminal amino acid was sequenced by Edams Hydrolysis, which shows that the first 15 amino acids on N-terminus were identical to those in SEQ ID NO: 2.

Example 6

Preparation of Antibody Against Human Galectin 15

The following specific human galectin 15 polypeptide was synthesized by a polypeptide synthesizer (PE-ABI): NH2-Met-Ser-Ser-Leu-Pro-Val-Pro-Tyr-Thr-Leu-Pro-Val-Ser-Leu-Pro-COOH (SEQ ID NO:7). The polypeptide was conjugated with hemocyanin and bovine serum albumin (BSA) respectively to form two composites (See Avrameas et al., Immunochemistry, 1969, 6:43). 4 mg of hemocyanin-polypeptide composite was used to immunize rabbit together with Freund's complete adjuvant. The rabbit was re-immunized with the hemocyanin-polypeptide composite and Freund's incomplete adjuvent 15 days later. The titer of antibody in the rabbit sera was determined with a titration plate coated with 15 μg/ml BSA-polypeptide composite by ELISA. The total IgG was isolated from the sera of an antibody positive rabbit with Protein A-Sepharose. The polypeptide was bound to Sepharose 4B column activated by cyanogen bromide. The antibodies against the polypeptide were isolated from the total IgG by affinity chromatography. The immunoprecipitation approved that the purified antibodies could specifically bind to human galectin 15.

We claim:

1. An isolated human galectin polypeptide having affinity with beta-galactose and comprising an amino acid sequence that has at least 98% identity with SEQ ID NO: 2.

2. The polypeptide of claim 1 wherein said polypeptide comprises the amino acid sequence of SEQ ID NO: 2.

3. A pharmaceutical composition comprising a polypeptide according to claim 1, and a pharmaceutically acceptable carrier.

* * * * *

SEQUENCE LISTING

```
<160> NUMBER OF SEQ ID NOS: 7

<210> SEQ ID NO 1
<211> LENGTH: 775
<212> TYPE: DNA
<213> ORGANISM: Homo sapiens
<220> FEATURE:
<221> NAME/KEY: CDS
<222> LOCATION: (225)..(644)
<223> OTHER INFORMATION:

<400> SEQUENCE: 1
ggctgcatta cagacacaga cctgcaaaca tctatggttg tgacagagtt tctttctgac     60
```

-continued

```
acctgagtct ttctcctgct gcacggaaag cttgctggga ggggcttgga atctggcatg      120
aagccaaagg gcatctctga gttgcagcat ttaaatgatc ccactcagag attcacacag      180
aagactggac acaattccga agagctgccc agaaggagag aaca atg tca tca cta      236
                                                 Met Ser Ser Leu
                                                  1 ccc gta cca tac aca ctg cct gtt tcc ttg cct gtt ggt tcg tgc gtg      284
Pro Val Pro Tyr Thr Leu Pro Val Ser Leu Pro Val Gly Ser Cys Val
 5              10                  15                  20 ata atc aca ggg aca ccg atc ctc act ttt gtc aag gac cca cag ctg      332
Ile Ile Thr Gly Thr Pro Ile Leu Thr Phe Val Lys Asp Pro Gln Leu
             25                  30                  35 gag gtg aat ttc tac act ggg atg gat gag gac tca gat att gct ttc      380
Glu Val Asn Phe Tyr Thr Gly Met Asp Glu Asp Ser Asp Ile Ala Phe
         40                  45                  50 caa ttc cga ctg cac ttt ggt cat cct gca atc atg aac agt tgt gtg      428
Gln Phe Arg Leu His Phe Gly His Pro Ala Ile Met Asn Ser Cys Val
     55                  60                  65 ttt ggc ata tgg aga tat gag gag aaa tgc tac tat tta ccc ttt gaa      476
Phe Gly Ile Trp Arg Tyr Glu Glu Lys Cys Tyr Tyr Leu Pro Phe Glu
 70                  75                  80 gat ggc aaa cca ttt gag ctg tgc atc tat gtg cgt cac aag gaa tac      524
Asp Gly Lys Pro Phe Glu Leu Cys Ile Tyr Val Arg His Lys Glu Tyr
 85                  90                  95                 100 aag gta atg gta aat ggc caa cgc att tac aac ttt gcc cat cga ttc      572
Lys Val Met Val Asn Gly Gln Arg Ile Tyr Asn Phe Ala His Arg Phe
            105                 110                 115 ccg cca gca tct gtg aag atg ctg caa gtc ttc aga gat atc tcc ctg      620
Pro Pro Ala Ser Val Lys Met Leu Gln Val Phe Arg Asp Ile Ser Leu
        120                 125                 130 acc aga gtg ctt atc agc gat tga gggagatgat cagactcctc attgttgagg      674
Thr Arg Val Leu Ile Ser Asp
        135 aatccctctt tctacctgac catgggattc ccagagccta ctaacagaat aatccctcct      734 caccccttcc cctacacttg atcattaaaa cagcaccaaa c                          775
```

<210> SEQ ID NO 2
<211> LENGTH: 139
<212> TYPE: PRT
<213> ORGANISM: Homo sapiens

<400> SEQUENCE: 2

```
Met Ser Ser Leu Pro Val Pro Tyr Thr Leu Pro Val Ser Leu Pro Val
 1               5                  10                  15

Gly Ser Cys Val Ile Ile Thr Gly Thr Pro Ile Leu Thr Phe Val Lys
                20                  25                  30

Asp Pro Gln Leu Glu Val Asn Phe Tyr Thr Gly Met Asp Glu Asp Ser
            35                  40                  45

Asp Ile Ala Phe Gln Phe Arg Leu His Phe Gly His Pro Ala Ile Met
        50                  55                  60

Asn Ser Cys Val Phe Gly Ile Trp Arg Tyr Glu Glu Lys Cys Tyr Tyr
 65                  70                  75                  80

Leu Pro Phe Glu Asp Gly Lys Pro Phe Glu Leu Cys Ile Tyr Val Arg
                85                  90                  95

His Lys Glu Tyr Lys Val Met Val Asn Gly Gln Arg Ile Tyr Asn Phe
           100                 105                 110

Ala His Arg Phe Pro Pro Ala Ser Val Lys Met Leu Gln Val Phe Arg
       115                 120                 125
```

```
Asp Ile Ser Leu Thr Arg Val Leu Ile Ser Asp
    130                 135

<210> SEQ ID NO 3
<211> LENGTH: 24
<212> TYPE: DNA
<213> ORGANISM: Artificial
<220> FEATURE:
<223> OTHER INFORMATION: (oligonucleotide primer)

<400> SEQUENCE: 3
ggctgcatta cagacacaga cctg                                          24

<210> SEQ ID NO 4
<211> LENGTH: 24
<212> TYPE: DNA
<213> ORGANISM: Artificial
<220> FEATURE:
<223> OTHER INFORMATION: (oligonucleotide primer)

<400> SEQUENCE: 4
gtttggtgct gttttaatga tcat                                          24

<210> SEQ ID NO 5
<211> LENGTH: 33
<212> TYPE: DNA
<213> ORGANISM: Artificial
<220> FEATURE:
<223> OTHER INFORMATION: (oligonucleotide primer)

<400> SEQUENCE: 5
cccccatgga tgtcatcact acccgtacca tac                                33

<210> SEQ ID NO 6
<211> LENGTH: 33
<212> TYPE: DNA
<213> ORGANISM: Artificial
<220> FEATURE:
<223> OTHER INFORMATION: (oligonucleotide primer)

<400> SEQUENCE: 6
catggatccc catcgctgat aagcactctg gtc                                33

<210> SEQ ID NO 7
<211> LENGTH: 15
<212> TYPE: PRT
<213> ORGANISM: Artificial
<220> FEATURE:
<223> OTHER INFORMATION: (partial sequence of SEQ ID NO.: 2)

<400> SEQUENCE: 7

Met Ser Ser Leu Pro Val Pro Tyr Thr Leu Pro Val Ser Leu Pro
1               5                   10                  15
```